United States Patent [19]

Matsuo et al.

[11] Patent Number: 5,036,081
[45] Date of Patent: Jul. 30, 1991

[54] CALCIUM ABSORPTION PROMOTER

[75] Inventors: Takao Matsuo, Kyoto; Hiroyuki Odaka, Osaka; Tsuyoshi Suzuki; Masao Tsuda, both of Hyogo, all of Japan

[73] Assignee: Takeda Chemical Industries, Ltd., Osaka, Japan

[21] Appl. No.: 396,696

[22] Filed: Aug. 22, 1989

[30] Foreign Application Priority Data

Aug. 22, 1988 [JP] Japan .................. 63-207724

[51] Int. Cl.$^5$ .................... A61K 31/44; A61K 31/70; A61K 31/38; A61K 31/34; A61K 31/16; A61K 31/135; A61K 31/13
[52] U.S. Cl. ........................ 514/336; 514/23; 514/438; 514/471; 514/579; 514/654; 514/655; 514/659
[58] Field of Search .................. 514/32, 25, 42, 43, 514/23, 438, 336, 471, 579, 654, 655, 659; 564/360, 363

[56] References Cited

U.S. PATENT DOCUMENTS 4,486,602 12/1984 Horii et al. ........................ 564/360
4,701,559 10/1987 Horii et al. ........................ 564/363
4,777,294 10/1988 Horii et al. ........................ 564/363

FOREIGN PATENT DOCUMENTS 0194794 9/1986 European Pat. Off. .

OTHER PUBLICATIONS

E. Truscheit, et al., "Chemistry and Biochemistry of Microbial a-Glucosidase Inhibitors", Angewandte Chemie International Edition in English, vol. 20 (9), pp. 744-761 (1981).

Primary Examiner—Frederick E. Waddell
Assistant Examiner—Raymond J. Henley, III
Attorney, Agent, or Firm—Wegner, Cantor, Mueller & Player

[57] ABSTRACT

Alpha-glucosidase inhibitor is provided as a promoter of calcium absorption in mammals. The examples of the inhibitor are shown by the formula;

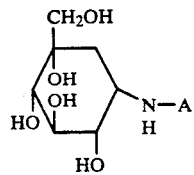

wherein A stands for a $C_1$–$C_{10}$ acyclic hydrocarbon group which may be substituted by hydroxyl, phenoxy, thienyl, furyl, pyridyl, cyclohexyl or phenyl group which itself may be further substituted, a $C_5$–$C_6$ cyclic hydrocarbon group which may be substituted by hydroxyl, hydroxymethyl, methyl or amino group, or a sugar residue.

There is also provided a calcium preparation which contains an α-glucosidase inhibitor and a calcium source.

4 Claims, No Drawings

CALCIUM ABSORPTION PROMOTER

This invention relates to a calcium absorption promoting drug comprising an α-glucosidase inhibitor substance which assists in the absorption of calcium from the digestive tract of mammalian animals.

Based on its calcium absorption promoting activity, the drug according to this invention finds application in the treatment of osteopenia, particularly osteoporosis, and other diseases.

Osteoporosis is a disease involving decrease in mass of bone caused by various etiological factors, and is a type of osteopenia. The mass of bone naturally decreases with advancing age but in osteoporosis, osteopenia is more marked and is often accompanied by such clinical manifestations as pain, arthralgia, gait disturbance, pathological bone fracture and so on.

In addition to the physiological factor of aging, various hormonal disturbances, particularly postmenopausal estrogen deficiency are considered as etiological factors. Still other conceivable causes are calcitonin deficiency, disorder of vitamin D metabolism and secondary hyperparathyroidism. Also involved are nutritional statuses including calcium deficiency and protein deficiency, the factor of exercise and race or species differences. Thus, osteoporosis is considered to be a disease caused by multiple factors. For the treatment of this disease, therefore, various types of drugs have been used for many years.

At present, the drugs used for the treatment of osteoporosis include estrogen, calcium preparations, calcitonin and vitamin D preparations. However, these drugs each have various problems, such as side effects, e.g. induction of genital bleeding, secondary hyperparathyroidism and acceleration of bone resorption, and necessity of massive drug administration.

As an etiologic factor in osteoporosis, there is a disorder of calcium metabolism. Thus, a shortage of calcium intake, a deficiency in calcium absorption from the intestinal tract, a decrease in blood calcium concentration due, at least in part, to an increased urinary excretion of calcium, and consequent onset of secondary hyperparathyroidism lead to osteoporosis. Calcium dynamics and balance studies on the rates of bone formation and bone resorption revealed that, compared with normal humans, many patients with osteoporosis show increased bone resorption over bone formation, suggesting that an excess in bone resorption over bone formation, that is to say a negative calcium balance, is a mechanism of onset of osteoporosis.

Based on the above fact, calcium supplementation is considered to be effective for the treatment of osteoporosis. Actually it is known that even in senile osteoporosis, administration of calcium preparations or ingestion of high-calcium diets leads to a positive calcium balance, while ingestion of low-calcium diets leads to a negative calcium balance.

The daily calcium intake recommended for adults by the Ministry of Health and Welfare of Japan is 600 milligrams but even if this amount of calcium is taken daily, the calcium balance is elderly subjects is generally negative because of poor absorption, thus defeating the expectation. The main reason is said to be the low absorption rate of calcium and this tendency is particularly pronounced in subjects of advanced age. Therefore, the development of a potent calcium absorption promoting agent is a pressing need.

The inventors of this application paid attention to α-glucosidase inhibitor substances and investigated their pharmacological activities. As a result, it was found that these substances have the ability to promote absorption of calcium from the alimentary canal of mammalian animals including humans, showing no side effect such as diarrhea, meteorism, etc. and suppressing increase in body weight.

Thus, by inhibiting α-glucosidase activity, such an inhibitor substance suppresses digestion of carbohydrates so as to increase the concentration of undigested carbohydrates in the alimentary canal of mammals. Such an increase in undigested carbohydrates triggers the production of lactic acid by the intestinal flora to render the inside of the alimentary canal acidic, thus providing an environment favoring dissolution of calcium. The above is a presumed mechanism for facilitated absorption of calcium from the alimentary canal.

As examples of the α-glucosidase inhibitor to be used in accordance with this invention, there may be mentioned valiolamine derivatives of the general formula

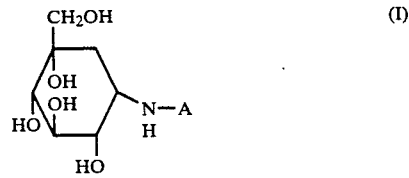

wherein A stands for a $C_{1-10}$ acyclic hydrocarbon group which may be substituted by hydroxyl, phenyl, thienyl, furyl, pyridyl, cyclohexyl and phenyl which itself may be further substituted, a $C_{5-6}$ cyclic hydrocarbon group which may be substituted by hydroxyl, hydroxymethyl, methyl and amino, or a sugar residue. These compounds are described in U.S. Pat. Nos. 4,701,559; 4,777,294 and 4,515,675.

Referring to the above general formula [I], A includes a $C_{1-10}$ straight chain or branched aliphatic hydrocarbon group which may be either saturated or unsaturated and may be substituted by hydroxy, phenoxy, thienyl, furyl, pyridyl, cyclohexyl, or phenyl which may be substituted. The substituents for the phenyl which may be substituted include, among others, lower ($C_{1-6}$) alkyl, lower ($C_{1-6}$) alkoxy, halogen, phenyl and so on.

Furthermore, A stands for a $C_{5-6}$ cyclic hydrocarbon group or a sugar residue. These groups may each have substituents such as hydroxy, hydroxymethyl, methyl, amino and so on. The term 'sugar residue' is used herein to mean the group available on elimination of one hydrogen atom from a carbohydrate molecule, and as such may stand for the residue derived from a monosaccharide or an oligosaccharide, for instance.

These derivatives may be used in the form of salts with inorganic acids, e.g. hydrochloric acid, or organic acids, e.g. citric acid.

The following is a partial list of N-substituted valiolamine derivatives of general formula [I].

(1) N-phenethylvaliolamine,
(2) N-(3-phenylallyl)valiolamine,
(3) N-furfurylvaliolamine,
(4) N-thenylvaliolamine,
(5) N-(3-pyridylmethyl)valiolamine,
(6) N-(4-bromobenzyl)valiolamine,
(7) N-[(R)-β-hydroxyphenethyl]valiolamine,
(8) N-[(S)-β-hydroxyphenethyl]valiolamine, (9) N-(β-hydroxy-2-methoxyphenethyl)valiolamine,
(10) N-(3,5-di-tert-butyl-4-hydroxybenzyl)valiolamine,
(11) N-(cyclohexylmethyl)valiolamine,
(12) N-geranylvaliolamine,
(13) N-(1,3-dihydroxy-2-propyl)valiolamine,
(14) N-(1,3-dihydroxy-1-phenyl-2-propyl)valiolamine,
(15) N-[(R)-α-(hydroxymethyl)benzyl]valiolamine,
(16) N-cyclohexylvaliolamine,
(17) N-(2-hydroxycyclohexyl)valiolamine,
(18) N-[(1R,2R)-2-hydroxycyclohexyl]valiolamine,
(19) N-(2-hydroxycyclopentyl)valiolamine,
(20) methyl 4-[(1S,2S)-(2,4,5(OH)/3,5)-2,3,4,5-tetrahydroxy-5-(hydroxymethyl)cyclohexyl]amino-4,6-dideoxy-α-D-glucopyranoside,
(21) methyl 4-[(1S,2S)-(2,4,5(OH)/3,5)-2,3,4,5-tetrahydroxy-5-(hydroxymethyl)cyclohexyl]amino-4-deoxy-α-D-glucopyranoside,
(22) [(1S,2S)-(2,4,5(OH)/3,5)-2,3,4,5-tetrahydroxy-5-(hydroxymethyl)cyclohexyl][(1R,2S)-(2,6/3,4)-4-amino-2,-3-dihydroxy-6-(hydroxymethyl)cyclohexyl]amine,
(23) N-[(1R,2S)-(2,4/3,5)-2,3,4-trihydroxy-5-(hydroxymethyl)cyclohexyl]valiolamine,
(24) N-[(1R,2S)-(2,6/3,4)-4-amino-2,3-dihydroxy-6-methylcyclohexyl]valiolamine,
(25) N-[(1R,2S)-(2,6/3,4)-2,3,4-trihydroxy-6-methylcyclohexyl]valiolamine,
(26) N-[(1R,2S)-(2,4,6/3)-2,3,4-trihydroxy-6-methylcyclohexyl]valiolamine,
(27) 4-O-α-[4-[((1S)-(1,2,4,5(OH)/3,5)-2,3,4,5-tetrahydroxy-5-(hydroxymethyl)cyclohexyl)amino]-4,6-dideoxy-D-glucopyranosyl]-D-glucopyranose, and
(28) 1,6-anhydro-4-O-α-[4-[((1S)-(1,2,4,5(OH)/3,5)-2,3,4,5-tetrahydroxy-5-C-(hydroxymethyl)cyclohexyl)amino]-4,6-dideoxy-D-glucopyranosyl]-β-D-glucopyranose.

Particularly suited for the purpose of this invention is N-(1,3-dihydroxy-2-propyl)valiolamine, i.e. 1(1S)-(1(OH),2,4,5,/1,3)-5[[2-hydroxy-1-(hydroxymethyl)ethyl]amino]-1-C-(hydroxymethyl)-1,2,3,4-cyclohexanetetrol.

An N-substituted derivative of valienamine of the general formula,

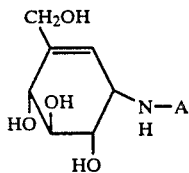

[II]

wherein A is a $C_{1-10}$ acyclic hydrocarbon group which may be substituted by hydroxyl, phenoxy, thienyl, furyl, pyridyl, cyclohexyl and/or phenyl which itself may also be substituted, a $C_{5-6}$ cyclic hydrocarbon group which may be substituted by hydroxyl, hydroxymethyl, methyl and/or amino, or a sugar residue, which is described in U.S. Pat. No. 4,486,602, and an N-substituted derivative of validamine of the general formula,

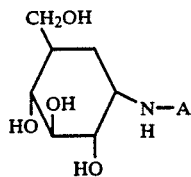

[III]

wherein A stands for a $C_{1-10}$ acyclic hydrocarbon group which may be substituted by hydroxyl, phenoxy, thienyl, furyl, pyridyl, cyclohexyl and/or phenyl group which itself may also be substituted, a $C_{5-6}$ cyclic hydrocarbon group which may be substituted by hydroxyl, hydroxymethyl, methyl and/or amino, or a sugar residue, which is described in U.S. Pat. Nos. 4,701,559 and 4,777,294 can also be used with advantage as α-glucosidase inhibitors according to this invention. Aside from the above compounds, the following compounds can also be used for the purposes of this invention.

Acarbose (BAY g 5421, Naturwissenschaften 64, 535–517, 1997, U.S. Pat. No. 4,062,950); trestain (J. Antibiotics 36, 1157–1175, 1983 and 37, 182–186, 1984 and U.S. Pat. No. 4,273,765), adiposins (J. Antibiotics 35, 1234–1236, 1982), J. Jap. Soc. Starch Sci 26, 134–144 (1979), 27, 107–113, 1980, Japanese Patent Application KOKAI No. 64509/1980, No. 123986/1981 and No. 125398/1981, and U.S. Pat. No. 4,197,292), *amylostatins* (Agric. Biol. Chem. 46, 1941–1945, 1982, Japanese Patent application KOKAI No. 71494/1980 and No. 157595/1980, and U.S. Pat. No. 4,010,258), *oligostatins* (SF-1130X, Japanese Patent Application KOKAI No. 26398/1978 and U.S. Pat. No. 4,316,894, J. Antibiotics 34, 1424–1433, 1981), and aminosugar compounds (U.S. Pat. No. 4,254,256).

Regarding the α-glucosidase inhibitors of microbial origin, inclusive of the above-mentioned compounds, a general review by E. Truscheit (Angewandte Chemie 93, 738–755, 1981) is available.

Furthermore, the compounds obtainable by methanolysis of acarbose or oligostatins C, i.e. methyl 4-[(1S,6S)-(4,6/5)-4,5,6-trihydroxy-3-hydroxymethyl-2-cyclohexen-1-yl]amino-4,6-dideoxy-α-D-glucopyranosides (182nd ACS National Meeting Abstracts Paper, MEDI 69, August 1981, New York, J. Antibiotics 34, 1429–1433, 1981, and Japanese Patent Application No. 24397/1982), 1-deoxynojirimycin (Naturwissenschaften 66, 584–585, 1979) and N-substituted derivatives thereof, for example, BAY m 1099 and BAY o 1248 (J. Clin. Invest. 14 (2-II), 47, 1984, Diabetologia 27 (2), 288A 346A and 323A, 1984) can also be employed in the practice of this invention.

It is already known that by their α-glucosidase inhibitory activity, these compounds are of use as medicines such as antidiabetic or antiobesity agents.

This invention is concerned with a pharmaceutical agent which can be used in osteopenia, particularly for the treatment of osteoporosis.

In accordance with this invention, such an α-glucosidase inhibitor can be formulated with various pharmaceutically acceptable vehicles or carriers and administered as a therapeutic drug. The contemplated route of administration is oral. Therefore, the therapeutic composition of this invention can also be administered in solid dosage forms including tablets, capsules and so on.

For the manufacture of a solid dosage form such as a tablet, there may be incorporated such materials as binders (for example, starch, hydroxypropylcellulose, hydroxymethylpropylmethylcellulose, etc.), disintegrating agents (for example, starch, carboxymethylcellulose calcium, low-substitution hydroxypropylcellulose, etc.), excipients (for example, lactose, starch, etc.) and so on.

Furthermore, the composition of this invention can be provided as a calcium preparation for supplying calcium to a subject, by adding a calcium source, for example, an enteric coated calcium source (e.g. calcium carbonate, calcium lactate etc.) and so forth.

The dosage of α-glucosidase inhibitors for the purposes of this invention may be comparatively small, although it varies with the administration route and the symptoms. For example, the dosage of valiolamine derivatives, which are among the α-glucosidase inhibitors mentioned above, is generally 0.01 to 100 mg, preferably 0.05 to 10 mg, and more preferably 0.1 to 2 mg per day per adult. This dosage is administered generally in 2 or 3 divided doses, preferably preprandially.

The valiolamine derivatives, e.g. N-(1,3-dihydroxy-2-propyl)valiolamine, which are used in the practice of this invention are highly safe compounds and their oral $LD_{50}$ values (acute toxicity) in mice (NRMI) and rats (Wistar) are 14.7–21.5 grams/kilogram (mice) and about 20 grams/kilogram (rats).

The composition of this invention in a very small dose promotes absorption of calcium from the alimentary canal of mammalian animals without enhancing bone resorption.

This means that unlike the conventional calcium preparation to be administered in a large amount, the composition insures sufficient calcium absorption with usual dietary intake. Having such a calcium absorption promoting potential, this composition is very effective in the prevention and treatment of osteopenia, particularly osteoporosis.

The following test and working examples are intended to illustrate this invention in further detail and should by no means be construed as limiting the scope of this invention.

TEST EXAMPLE 1

Dietary calcium absorption promoting effect of N-(1,3-dihydroxy-2-propyl)valiolamine in rats Five-week-old male rats (Jcl: SD) were divided into 2 groups and one group (control group) was given a regular diet (CE-2. Japan Clea Co.) while the other group was put on a medicated diet, i.e. CE-2 supplemented with N-(1,3-dihydroxy-2-propyl)valiolamine (AO-128). The level of addition of AO-128 was 10 ppm during the first 10 days and 25 ppm during the subsequent 7 days. On days 3, 10 and 17 of feeding, the body weight, food consumption, urinary calcium excretion, and plasma calcium concentration were determined. The results are shown in Table 1.

TABLE 1

| Number of animals | Control group 5 | AO-128 group 6 |
|---|---|---|
| Body weight (g) | | |
| Initial | 115 ± 4 | 115 ± 3 |
| Day 3 | 145 ± 5 | 143 ± 7 |
| Day 10 | 181 ± 10 | 176 ± 8 |
| Day 17 | 259 ± 22 | 250 ± 14 |
| Food consumption (g/day) | | |
| Day 3 | 15.6 ± 0.7 | 12.7 ± 1.7* |
| Day 10 | 22.0 ± 2.0 | 22.7 ± 2.3 |
| Day 17 | 22.5 ± 2.2 | 24.5 ± 2.0 |

TABLE 1-continued

| Number of animals | Control group 5 | AO-128 group 6 |
|---|---|---|
| Urinary calcium (mg/day) | | |
| Day 3 | 0.90 ± 0.37 | 1.99 ± 0.67** |
| Day 10 | 0.53 ± 0.10 | 2.10 ± 0.54** |
| Day 17 | 0.55 ± 0.12 | 2.78 ± 1.11 |
| Plasma calcium (mg/dl) | | |
| Day 3 | 10.0 ± 0.5 | 10.8 ± 0.5 |
| Day 10 | 10.1 ± 0.8 | 10.3 ± 0.5 |
| Day 17 | 9.7 ± 0.2 | 9.9 ± 0.3 |

Each value represents the mean ±S.D. The symbols * and ** mean 5 and 1% levels of significance, respectively, both compared with the control group.

In the AO-128 group, a tendency of suppressed body weight gain was noted. The food consumption of this group showed a slight decrease on day 3 but showed recovery on day 10 and, rather, a tendency of increase in day 17. The urinary calcium excretion showed increases in the AO-128 group on all determination days but no significant change was found in plasma calcium concentration.

TEST EXAMPLE 2

Exogenous calcium absorption promoting effect of N-(1,3-dihydroxy-2-propyl)valiolamine in rats Eight-week-old male rats (Jcl: SD) fasted for 20 hours were orally dosed with 72.5% sucrose aqueous solution [2.5 g (sucrose)/kg (body weight)], 5% calcium carbonate aqueous suspension [400 mg ($CaCO_3$)/kg (body weight)] and 0.015, 0.05 or 0.15% aqueous AO-128 solution [0.3, 1.0 or 3.0 mg ((AO-128)/kg (body weight)] and the 24 hr urine was collected for the determination of urinary calcium. The animals were deprived of food during urine collection but had free access to water. The results are shown in Table 2.

TABLE 2

| Sucrose (g/kg) | Calcium carbonate (mg/kg) | AO-128 (mg/kg) | Number of animals | Urinary calcium (μg/day) |
|---|---|---|---|---|
| 0 | 0 | 0 | 5 | 210 ± 87 |
| 2.5 | 400 | 0 | 6 | 151 ± 42 |
| 2.5 | 400 | 0.3 | 7 | 311 ± 214 |
| 2.5 | 400 | 1.0 | 6 | 441 ± 172* |
| 2.5 | 400 | 3.0 | 6 | 517 ± 195** |

Each value represents the mean±S.D. The symbols * and ** stand for 2 and 1% levels of significance, respectively, both compared with the control group.

Whereas the addition of calcium carbonate and sucrose caused no increase in urinary calcium excretion, the concurrent addition of AO-128 caused a dose-dependent increase in urinary calcium.

Based on the above results of the two experiments, it is considered that AO-128 increases the absorption of calcium when it is administered concurrently with a carbohydrate and calcium.

TEST EXAMPLE 3

Effect of N-(1,3-dihydroxy-2-propyl)valiolamine and 1,25$(OH)_2$ vitamin $D_3$ on bone resorption The bone resorption rate was determined by the method of Raisz (J. Clin. Invest. 44, 103–116, 1965). Thus, one Sprague-Dawley rat on day 18 of gestation was subcutaneously dosed with 50 μCi of $^{45}Ca$ (an isotope of calcium, in $CaCl_2$) and laparotomy was performed on the next day. The fetuses were aseptically taken out and under a dissecting microscope, the bilateral antebrachial bones (radius and ulna) of a fetus were cut off from the trunk. The connective tissues and cartilages were removed as much as possible to prepare a sample for bone culture. Each piece of bone was cultured in 0.6 ml of BGJ$_b$ medium (Fitton-Jackson modification, GIBCO Laboratories, U.S.A., supplemented with 2 mg/ml of bovine serum albumin) at 37° C. for 24 hours and after addition of AO-128 at a final concentration of 10 μg/ml or 1,25(OH)$_2$ vitamin D$_3$ at a concentration of 0.8 pg/ml, was further incubated in the same medium for 2 days. The $^{45}$Ca radioactivity in the medium and that in the bone were respectively counted and the rate (%) of $^{45}$Ca release from the bone into the medium was calculated by means of the following equation.

$$\text{Rate (\%) of }^{45}\text{Ca released from bone to medium} = \frac{^{45}\text{Ca count in medium}}{^{45}\text{Ca count in medium} + ^{45}\text{Ca count in bone}} \times 100$$

The bones from another fetus of the same litter were incubated without addition of the test compounds for 2 days as controls. The means±S.D. of values found from 5 pieces of bone in each group was calculated and the percentage (%) of the mean value relative to the mean value of the control group was calculated. The results are shown in Table 3.

TABLE 3

|  | $^{45}$Ca released into medium (%) |
|---|---|
| Control | 12.7 ± 3.2 |
| AO-128 (10 μg/ml) | 12.6 ± 2.5 |
|  | Mean ± S.D. (n = 5) |
| Control | 12.3 ± 2.2 |
| 1,25(OH)$_2$ vitamin D$_3$ (0.8 pg/ml) | 26.6 ± 2.2* |
|  | Mean ± S.D. (n = 5) |

*p < 0.001

Comparison of 1,25(OH)$_2$ vitamin D$_3$, which is currently used as a therapeutic drug for osteoporosis, with AO-128, which is one of the/α-glucosidase inhibitors according to this invention, in the effect on bone resorption revealed that whereas no change occurred with 10 μg/ml of AO-128, 0.8 pg/ml of 1,25(OH)$_2$ vitamin D$_3$ caused a 2.2-fold increase in the release of $^{45}$Ca into the medium. The above results suggested that the α-glucosidase inhibitor of this invention promotes absorption of calcium without enhancing the bone resorption which is undesirable in osteoporosis.

EXAMPLE 1

The following components were blended and processed into oral tablets by the established pharmaceutical procedure.

| N-(1,3-Dihydroxy-2-propyl)valiolamine | 0.05 mg |
|---|---|
| Corn starch | 30 mg |
| Lactose | 76.65 mg |
| Hydroxypropylcellulose | 3.0 mg |
| Magnesium stearate | 0.3 mg |
| Total | 110.0 mg (per tablet) |

EXAMPLE 2

Tablets were prepared in the same manner as Example 1 employing the following components;

| N-(1,3-Dihydroxy-2-propylvaliolamine | 0.05 mg |
|---|---|
| Precipitated calcium carbonate | 250.8 mg (Ca content: 100 mg) |
| Lactose | 131.65 mg |
| Corn starch | 100 mg |
| Hydroxypropylcellulose | 15 mg |
| Magnesium stearate | 2.5 mg |
| Total | 500 mg (per tablet) |

We claim:

1. A method for promoting calcium absorption which comprises administering orally an effective inhibiting amount of an α-glucosidase inhibitor substance to a mammal in need thereof, wherein said inhibitor substance is a compound of the formula:

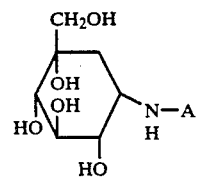

wherein A is selected from the group consisting of:
a C$_1$–C$_{10}$ acyclic hydrocarbon group which is unsubstituted or substituted by at least one member selected from the group consisting of hydroxyl, phenoxy, thienyl, furyl, pyridyl, cyclohexyl, phenyl, C$_{1-6}$-alkylphenyl, C$_{1-6}$-alkoxyphenyl, halophenyl and biphenyl;
a C$_5$–C$_6$ cyclic hydrocarbon group which is unsubstituted or substituted by at least one member selected from the group consisting of hydroxyl, hydroxymethyl, methyl and amino; and
a sugar residue.

2. A method for promoting calcium absorption according to claim 1 wherein said inhibitor substance is preprandially administered in an amount of 0.01 to 100 mg per day per adult human.

3. A method of treating osteopenia, which comprises administering orally an effective inhibiting amount of an α-glucosidase inhibitor substance to a mammalian animal, wherein said inhibitor substance is a compound of the formula:

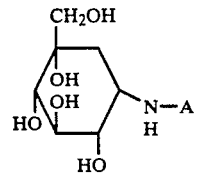

wherein A is selected from the group consisting of:
a C$_1$–C$_{10}$ acyclic hydrocarbon group which is unsubstituted or substituted by at least one member selected from the group consisting of hydroxyl, phenoxy, thienyl, furyl, pyridyl, cyclohexyl, phenyl, C$_{1-6}$-alkylphenyl, C$_{1-6}$-alkoxyphenyl, halophenyl and biphenyl;
a C$_5$–C$_6$ cyclic hydrocarbon group which is unsubstituted or substituted by at least one member selected from the group consisting of hydroxyl, hydroxymethyl, methyl and amino; and
a sugar residue.

4. A method according to claim 3, wherein said α-glucosidase inhibitor is N-(1,3-dihydroxy-2-propyl)valiolamine.

* * * * *